(12) United States Patent
Maki

(10) Patent No.: US 9,028,428 B2
(45) Date of Patent: May 12, 2015

(54) MEDICAL GUIDEWIRE

(75) Inventor: Hideaki Maki, Seto (JP)

(73) Assignee: Asahi Intecc Co., Ltd., Nagoya-shi (JP)

( * ) Notice: Subject to any disclaimer, the term of this patent is extended or adjusted under 35 U.S.C. 154(b) by 358 days.

(21) Appl. No.: 13/438,351

(22) Filed: Apr. 3, 2012

(65) Prior Publication Data

US 2012/0265100 A1 Oct. 18, 2012

(30) Foreign Application Priority Data

Apr. 18, 2011 (JP) ................................. 2011-091644

(51) Int. Cl.
*A61M 25/09* (2006.01)

(52) U.S. Cl.
CPC ..... *A61M 25/09* (2013.01); *A61M 2025/09083* (2013.01); *A61M 2025/09175* (2013.01)

(58) Field of Classification Search
CPC ......... A61M 2025/09083; A61M 2025/09175; A61M 25/09
USPC ....................................................... 600/585
See application file for complete search history.

(56) References Cited

U.S. PATENT DOCUMENTS

| 4,771,788 | A * | 9/1988 | Millar .......................... 600/455 |
| 5,345,945 | A | 9/1994 | Hodgson et al. |
| 5,954,672 | A | 9/1999 | Schwager |
| 8,758,269 | B2 * | 6/2014 | Miyata et al. ................. 600/585 |
| 2003/0181828 | A1 * | 9/2003 | Fujimoto et al. ............. 600/585 |
| 2004/0122340 | A1 * | 6/2004 | Vrba et al. .................... 600/585 |
| 2004/0167442 | A1 | 8/2004 | Shireman et al. |
| 2004/0167443 | A1 | 8/2004 | Shireman et al. |
| 2005/0145307 | A1 | 7/2005 | Shireman et al. |
| 2005/0154371 | A1 | 7/2005 | Miyata et al. |
| 2006/0111649 | A1 | 5/2006 | Zhou |
| 2007/0123805 | A1 | 5/2007 | Shireman et al. |
| 2008/0004546 | A1 | 1/2008 | Kato |
| 2008/0234606 | A1 * | 9/2008 | Itou .............................. 600/585 |
| 2008/0281396 | A1 * | 11/2008 | Ishida et al. ................. 623/1.11 |
| 2009/0005706 | A1 | 1/2009 | Miyata et al. |
| 2009/0036832 | A1 | 2/2009 | Skujins et al. |
| 2009/0182246 | A1 * | 7/2009 | Kinoshita et al. ............ 600/585 |
| 2009/0299332 | A1 | 12/2009 | Shireman |

(Continued)

FOREIGN PATENT DOCUMENTS

| CN | 101674861 A | 3/2010 |
| EP | 1767239 A1 | 3/2007 |

(Continued)

OTHER PUBLICATIONS

Jul. 5, 2012 Search Report issued in European Patent Application 12159696.9.

(Continued)

*Primary Examiner* — Adam J Eiseman
*Assistant Examiner* — Patrick Fernandes
(74) *Attorney, Agent, or Firm* — Oliff PLC

(57) ABSTRACT

A guidewire includes a core shaft, an outer coiled body covering at least a portion of the core shaft, and an inner coiled body positioned between the outer coiled body and the core shaft. The inner coiled body covers the at least a portion of the core shaft and a resin material is filled between the inner coiled body and one of the outer coiled body and the core shaft to form a resin layer. Preferably, a space between the inner coiled body and the other of the outer coiled body and the core shaft is not filled with the resin material.

9 Claims, 7 Drawing Sheets

(56) References Cited

U.S. PATENT DOCUMENTS

| | | | |
|---|---|---|---|
| 2010/0004561 A1* | 1/2010 | Nabeshima | 600/585 |
| 2010/0318001 A1* | 12/2010 | Miyata et al. | 600/585 |
| 2010/0318065 A1* | 12/2010 | Miyata et al. | 604/526 |
| 2011/0319872 A1 | 12/2011 | Kawasaki | |
| 2012/0016463 A1 | 1/2012 | Ishida et al. | |

FOREIGN PATENT DOCUMENTS

| | | |
|---|---|---|
| EP | 1872821 A1 | 1/2008 |
| EP | 2 263 736 A1 | 12/2010 |
| JP | A-10-328309 | 12/1998 |
| JP | A-11-276596 | 10/1999 |
| JP | A-2005-185386 | 7/2005 |
| JP | A-2005-270466 | 10/2005 |
| JP | A-2006-519069 | 8/2006 |
| JP | A-2008-11938 | 1/2008 |
| JP | 2008520347 A | 6/2008 |
| JP | A-2009-337 | 1/2009 |
| JP | A-2009-112373 | 5/2009 |
| JP | A-2010-214054 | 9/2010 |
| JP | A-2010-535583 | 11/2010 |

OTHER PUBLICATIONS

Jun. 3, 2013 Notification of Reason for Refusal issued in Japanese Patent Application No. 2011-091644 (with English translation).

Jan. 11, 2013 Office Action issued in Japanese Patent Application No. 2011-091644 (with English Translation).

Sep. 12, 2014 Office Action issued in Japanese Application No. 2013-242942 (with translation).

Nov. 5, 2014 Office Action issued in Japanese Application No. 2013-242942.

Nov. 5, 2014 Office Action issued in Chinese Application No. 201210023410.9.

Dec. 19, 2014 Office Action issued in European Application No. 12 159 696.9-1506.

* cited by examiner

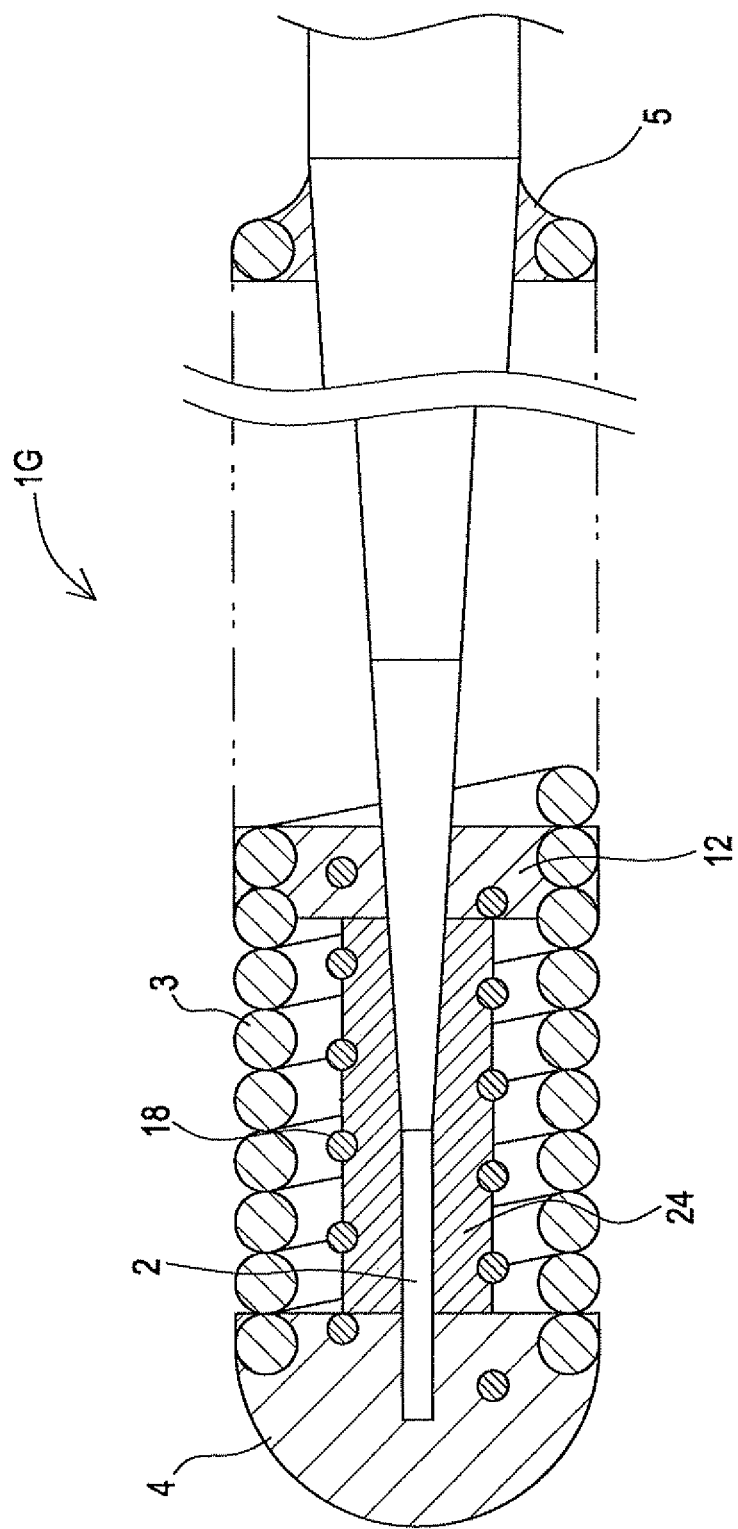

MEDICAL GUIDEWIRE

CROSS REFERENCE TO RELATED APPLICATION

This application claims priority to Japanese Patent Application No. 2011-091644 filed with the Japan Patent Office on Apr. 18, 2011, the entire contents of which are hereby incorporated by reference.

BACKGROUND

The disclosed embodiments relate to a medical device. More particularly, the disclosed embodiments relate to a guidewire suitably used in a medical field.

A medical guidewire is used, for example, as a guide for inserting a catheter into a vessel, a ureter, or an organ. The medical guidewire is also used as a guide for inserting a body-indwelling device into a vessel where an aneurysm is formed. The medical guidewire usually includes a core shaft and a coiled body that is wound around the outer circumferential surface of a front end portion of the core shaft. The medical guidewire also includes a most distal portion formed by joining a front end portion of the coiled body and the front end portion of the core shaft.

The medical guidewire disclosed in U.S. Pat. No. 5,345,945 includes an outer coil and an inner coil arranged inside the outer coil. The medical guidewire having such a configuration is provided with both flexibility and rotational force transmissibility at the front end portion.

The medical guidewire disclosed in JP-A-2010-214054 includes a core wire and a coil spring. In this medical guidewire, resin is filled inside the coil spring, that is, between the core wire and the coil spring. Such filling of resin improves the bonding strength between the core wire and the coil spring.

SUMMARY

However, when the front end portion of the medical guidewire disclosed in U.S. Pat. No. 5,345,945 is bent or curved while in use, the outer coil and the inner coil interfere with each other. Therefore, the outer coil and the inner coil may be deformed, or a coil strand of the inner coil may be overlaid on a coil strand of the outer coil. As a result, the front end portion of the medical guidewire may be damaged. When the front end portion of the medical guidewire is bent or curved, the inner coil and the core shaft similarly interfere with each other. As a result, for example, the core shaft may be broken, thereby deforming the inner coil. Furthermore, the interference between the inner coil and the outer coil may also result in the deformation of the outer coil.

In the medical guidewire disclosed in JP-A-2010-214054, resin is filled between the outer coiled body and the core shaft. This solves the problem of mutual interference between the outer coiled body and the core shaft. However, such resin hardens the front end portion of the medical guidewire more than necessary. As a result, the flexibility of the front end portion of the medical guidewire is lost, and thus such guidewire is prone to damaging an organ, such as a vessel.

In view of the above circumstances, an object of the present invention is to provide a medical guidewire having flexibility and robustness. More specifically, an object of the present invention is to prevent the damage of the front end portion of the medical guidewire by providing the medical guidewire, including the outer coil and the inner coil, with a structure for preventing the mutual interference between the outer coil and the inner coil or between the inner coil and the core shaft when the front end portion is bent or curved.

A medical guidewire according to embodiments of the present invention includes: a core shaft; an outer coiled body covering at least a front end portion of the core shaft; and an inner coiled body positioned inside the outer coiled body and covering at least the front end portion of the core shaft, wherein a resin material is filled between the outer coiled body and the inner coiled body or between the core shaft and the inner coiled body to form a resin layer.

BRIEF DESCRIPTION OF THE DRAWINGS

The foregoing and other objects, features, aspects and advantages of the invention will become more apparent from the following detailed description when taken in conjunction with the accompanying drawings.

FIG. 7 is an explanatory drawing of a medical guidewire according to a seventh embodiment.

DETAILED DESCRIPTION OF EMBODIMENTS

Figure 1:
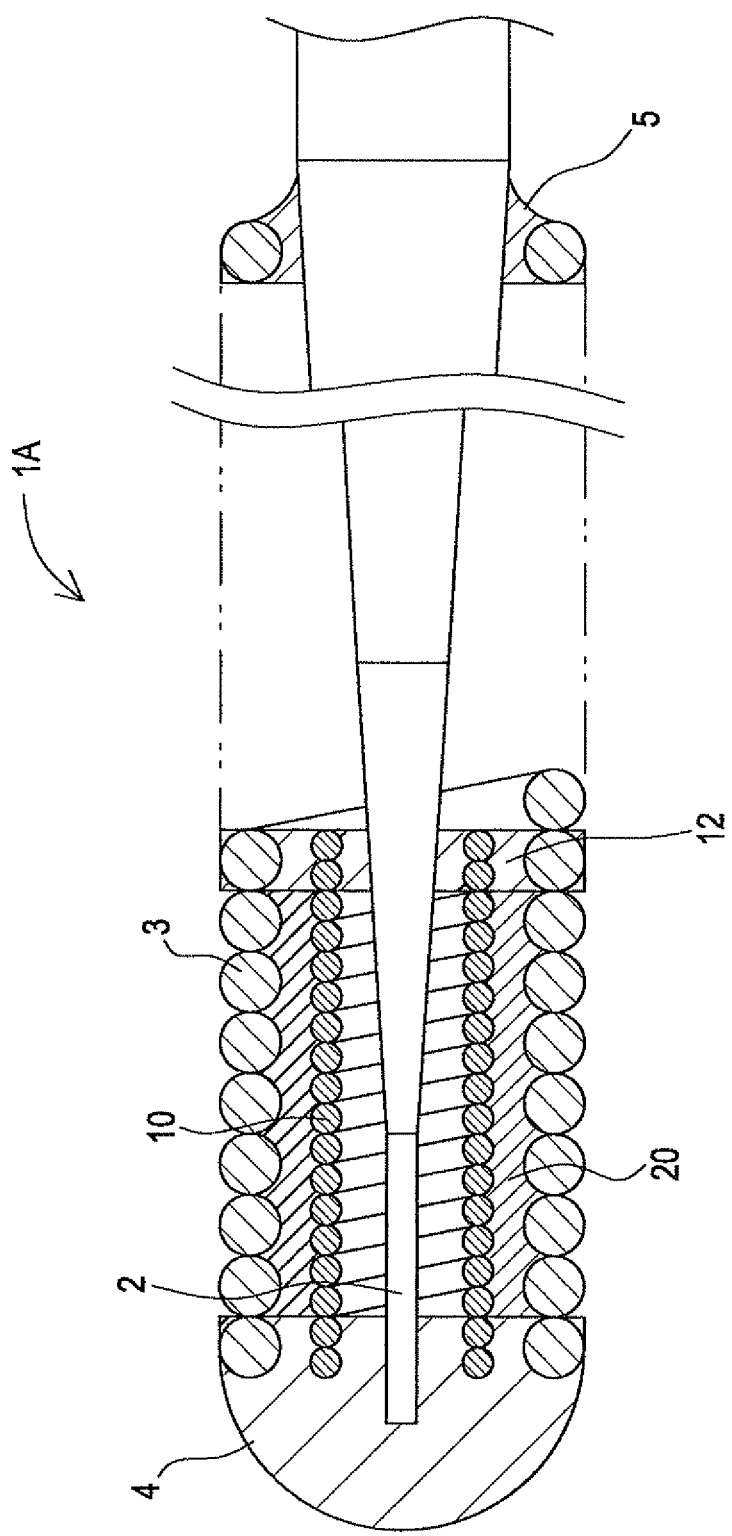
FIG. 1 is an explanatory drawing of a medical guidewire according to a first embodiment.

Preferred embodiments of the present invention are described below with reference to the accompanying drawings, in which like reference characters designate similar or identical parts throughout the several views thereof.

A medical guidewire according to embodiments of the present invention includes: a core shaft; an outer coiled body covering at least a front end portion of the core shaft; and an inner coiled body positioned inside the outer coiled body and covering at least the front end portion of the core shaft, wherein a resin material is filled between the outer coiled body and the inner coiled body or between the core shaft and the inner coiled body to form a resin layer.

In the case where the resin layer is formed between the outer coiled body and the inner coiled body, the outer coiled body and the inner coiled body may be severely bent or curved in use. However, the resin layer present between the outer coiled body and the inner coiled body prevents contact therebetween. Therefore, damage (for example, deformation) of the outer coiled body and the inner coiled body, caused by the mutual interference between the coiled bodies, is prevented. In this case, the inner coiled body and the core shaft may also be severely bent or curved and come into contact with each other. However, since the inner coiled body is fixed to the outer coiled body via the resin layer, the inner coiled body can be prevented from being deformed even upon contact with the bent or curved core shaft. At the same time, the presence of the inner coiled body prevents the core shaft from being excessively bent or curved. As a result, the bending or curvature of the core shaft is appropriately suppressed. This can also prevent the damage of the core shaft. In the case where the resin layer is formed between the inner coiled body and the core shaft, the resin layer present between the inner coiled body and the core shaft prevents the contact therebetween even when the inner coiled body and the core shaft are severely bent or curved in use. This can prevent, for example, the core shaft from being broken or damaged by the mutual interference between the inner coiled body and the core shaft. Therefore, the damage of the front end portion of the medical guidewire is prevented. Since the resin layer is present between the outer coiled body and the inner coiled body or between the inner coiled body and the core shaft, the front end portion of the medical guidewire does not become too hard. This ensures the flexibility of the front end portion of the medical guidewire. Therefore, according to embodiments of the present invention, the flexibility and robustness of the front end portion of the medical guidewire are improved.

At least the portion of the inner coiled body corresponding to the resin layer is preferably formed in a close coiled manner.

In the configuration of the medical guidewire described above, the close coiled portion of the inner coiled body has almost no gap between the coil strands. In the case where the resin layer is formed between the outer coiled body and the inner coiled body, therefore, the resin material can be prevented from leaking to the inside of the inner coiled body. This makes it possible to form the resin layer by reliably retaining the resin material outside the inner coiled body. Therefore, the mutual interference between the outer coiled body and the inner coiled body can reliably be prevented. In the case where the resin layer is formed between the inner coiled body and the core shaft, the resin material to be filled therebetween can be prevented from leaking to the outside of the inner coiled body. As described above, the coil strands of the inner coiled body are close coiled. Therefore, even when the outer coiled body and the inner coiled body are interfering with each other, the coil strand of the inner coiled body is prevented from being overlaid on the coil strand of the outer coiled body. Therefore, the close coiled coil strands make it possible to form the resin layer inside the inner coiled body.

This can also prevent the mutual interference between the inner coiled body and the core shaft. Furthermore, the mutual interference between the outer coiled body and the inner coiled body can reliably be prevented.

In the case where the resin layer is formed between the outer coiled body and the inner coiled body, the portion of the outer coiled body corresponding to the resin layer may preferably include a part formed in an open coiled manner.

As described above, in the case where the resin layer is formed between the outer coiled body and the inner coiled body, it is possible to easily fill the resin material between the outer coiled body and the inner coiled body through the gap between the coil strands of the outer coiled body. Therefore, the resin layer can smoothly be formed. As a result, the productivity of the medical guidewire is improved.

At least one of the outer coiled body and the inner coiled body is preferably a multiple-strand coil.

The multiple-strand coil has minimal so-called strand shift even when it is curved. In other words, the multiple-strand coil has originally a high robustness. Therefore, in the case where at least one of the outer coiled body and the inner coiled body in the medical guidewire according to embodiments of the present invention is a multiple-strand coil, the robustness of the front end portion of the medical guidewire is improved in addition to the improvement in robustness caused by the formation of the resin layer. In the case where the inner coiled body is formed of the multiple-strand coil and the outer coiled body is formed of the single coil, for example, the medical guidewire provided with such a multiple-strand coil exhibits at least the following advantages, compared to the medical guidewire including only the single coil. That is, the angle of winding the coil strand of the multiple-strand coil relative to the central axis of the medical guidewire is smaller than the angle of winding the coil strand of the single coil relative to the central axis of the medical guidewire. In the medical guidewire including the multiple-strand coil, therefore, the mutual interference between the coil strand of the outer coiled body and the coil strand of the inner coiled body is prevented. This can prevent the coil strand of the inner coiled body from being overlaid on the coil strand of the outer coiled body. Furthermore, the damage of the inner coiled body and the outer coiled body can be prevented. As a result, the robustness of the medical guidewire is improved.

The resin material is preferably hydrophobic.

The use of the hydrophobic resin material prevents the increase in volume of the resin layer, which would otherwise be caused by fluid such as bodily fluid. Therefore, the dimensional stability of the resin layer is ensured, while the robustness of the medical guidewire can be improved.

As described above, the configuration of the medical guidewire according to embodiments of the present invention can prevent, when the guidewire is bent or curved, the mutual interference between the outer coiled body and the inner coiled body or between the inner coiled body and the core shaft. Therefore, the damage of the front end portion of the medical guidewire can be prevented. As a result, the robustness of the front end portion of the medical guidewire is improved. In addition, in the configuration of the medical guidewire according to embodiment of the present invention, the resin layer is provided between the outer coiled body and the inner coiled body or between the inner coiled body and the core shaft. Therefore, the front end portion of the medical guidewire maintains an appropriate hardness. As a result, the guidewire according to embodiments of the present invention has also an effect of ensuring the flexibility of the front end portion of the medical guidewire.

Medical guidewires according to the first to seventh embodiments of the present invention will be described with reference to the accompanying drawings.

As illustrated in FIG. 1, a medical guidewire 1A includes a tapered core shaft 2 with a circular cross section. In other words, the core shaft 2 includes a front side having a small diameter and a proximal side having a large diameter.

An outer coiled body 3 is fixed to at least a front end portion of the core shaft 2. More specifically, the outer coiled body 3 is formed of a single coil in which at least the front end portion is formed in a close coiled manner. The front end of the outer coiled body 3 and the front end of the core shaft 2 are connected to form a substantially hemispherical most distal portion 4. The proximal end of the outer coiled body 3 is fixed to the core shaft 2 via a first fixing portion 5.

An inner coiled body 10 is arranged inside the outer coiled body 3, that is, between the outer coiled body 3 and the core shaft 2. The inner coiled body 10 covers at least the front end portion of the core shaft 2. The inner coiled body 10 is formed of a single coil which is close coiled over its entire length. The front end of the inner coiled body 10 is connected to the most distal portion 4. The proximal end of the inner coiled body 10 is connected to a second fixing portion 12 that continues to the core shaft 2 and the outer coiled body 3. The first fixing portion 5 and the second fixing portion 12 are formed using a variety of fixing techniques, including, but not limited to, adhesives, brazing, or welding.

Furthermore, a space extending from the most distal portion 4 to the second fixing portion 12 is formed between the outer coiled body 3 and the inner coiled body 10. A resin material is filled in this space to thereby form a resin layer 20.

Preferable examples of the resin material include, but are not particularly limited to, various hydrophobic resin materials. Examples of the hydrophobic resin material include rubber materials such as silicon rubber and acrylic rubber, elastomer materials such as polyurethane-based elastomer and polyamide-based elastomer, and fluororesin materials such as a tetrafluoroethylene-hexafluoropropylene copolymer.

In the case where a hydrophilic resin material is used as the resin material in forming the resin layer 20 between the outer coiled body 3 and the inner coiled body 10, the resin layer 20 absorbs water and becomes swollen upon exposure to water. This increases the volume of the resin layer 20. As a result, the swollen resin layer 20 presses the outer coiled body 3 outward in the radial direction. The swollen resin layer 20 also presses the inner coiled body 10 toward the central axis of the medical guidewire 1A. As a result, the pressed outer coiled body 3 and inner coiled body 10 may be deformed. To prevent the deformation, the hydrophobic resin material described above is preferably used as the resin material forming the resin layer 20.

The resin layer 20 is formed, for example, as follows. That is, a resin material is heated and melted, and the molten resin material is poured into or pushed out of the space between the outer coiled body 3 and the inner coiled body 10. Alternatively, a solution obtained by dissolving the resin material in a solvent is applied to a portion where the resin layer 20 is to be formed, and then the solvent is dried. The method for forming the resin layer 20 is not limited to the above examples, and other techniques can also suitably be used.

The resin layer 20 between the outer coiled body 3 and the inner coiled body 10 is formed, for example, as follows. That is, a molten or dissolved resin material is poured from outside the outer coiled body 3. Alternatively, before the most distal portion 4 is formed, the resin material is poured between the outer coiled body 3 and the inner coiled body 10 through an opening formed on the front side in the axial direction of the outer coiled body 3 and the inner coiled body 10. Further alternatively, the resin layer 20 may be formed by pushing the resin material out of the front side.

The medical guidewire 1A having the above configuration includes the resin layer 20 interposed between the outer coiled body 3 and the inner coiled body 10. With this configuration, the outer coiled body 3 and the inner coiled body 10 do not come into contact with each other even when the outer coiled body 3 and the inner coiled body 10 are severely bent or curved in use. This prevents, for example, damage, such as the deformation of the outer coiled body 3 and the inner coiled body 10, that would otherwise be caused by the mutual interference between the outer coiled body 3 and the inner coiled body 10 while the guidewire is in use. As a result, the damage of the front end portion of the medical guidewire 1A is prevented. In addition, the robustness of the front end portion of the medical guidewire 1A is improved. When the inner coiled body 10 and the core shaft 2 are severely bent or curved, the core shaft 2 may come into contact with the inner coiled body 10. In this case, the deformation of the inner coiled body 10, caused by the bent or curved core shaft 2, can be prevented since the inner coiled body 10 is fixed to the outer coiled body 3 via the resin layer 20. At the same time, the inner coiled body 10 suitably prevents the core shaft 2 from being further bent or curved. Therefore, the damage of the core shaft 2 can also be prevented. In one embodiment, the resin layer 20 is provided only between the outer coiled body 3 and the inner coiled body 10. That is, resin is not provided between the core shaft 2 and the inner coiled body 10. This prevents the front end of the medical guidewire 1A from becoming too hard. As a result, the front end of the medical guidewire 1A can maintain an appropriate flexibility.

Furthermore, a portion of the inner coiled body 10 corresponding to the resin layer 20 is formed in a close coiled manner. At that portion, therefore, there is almost no gap between the coil strands. This prevents the resin material, that fills a region between the outer coiled body 3 and the inner coiled body 10 from leaking to the inside of the inner coiled body 10. Therefore, the resin material is reliably retained outside the inner coiled body 10. This makes it possible to form the stable resin layer 20. As described above, the coil strands of the inner coiled body 10 are close coiled. Even when the outer coiled body 3 and the inner coiled body 10 interfere with each other, therefore, the coil strand of the inner coiled body 10 is prevented from being overlaid on (i.e., prevented from contacting) the coil strand of the outer coiled body 3. Therefore, the resin layer 20 can reliably be formed outside the inner coiled body 10. Also, the mutual interference between the inner coiled body 10 and the core shaft 2 can be prevented. Furthermore, the mutual interference between the outer coiled body 3 and the inner coiled body 10 can reliably be prevented. Note that the inner coiled body 10 according to the first embodiment is close coiled over its entire length in the axial direction. However, the close coiled portion is not limited to this example. For example, in one embodiment only the portion of the inner coiled body 10 corresponding to the resin layer 20 may be formed in a close coiled manner.

A medical guidewire 1B according to the second embodiment will be described below with reference to FIG. 2. The same elements as those in the first embodiment are denoted with the same reference signs and the description thereof is omitted.

Figure 2:
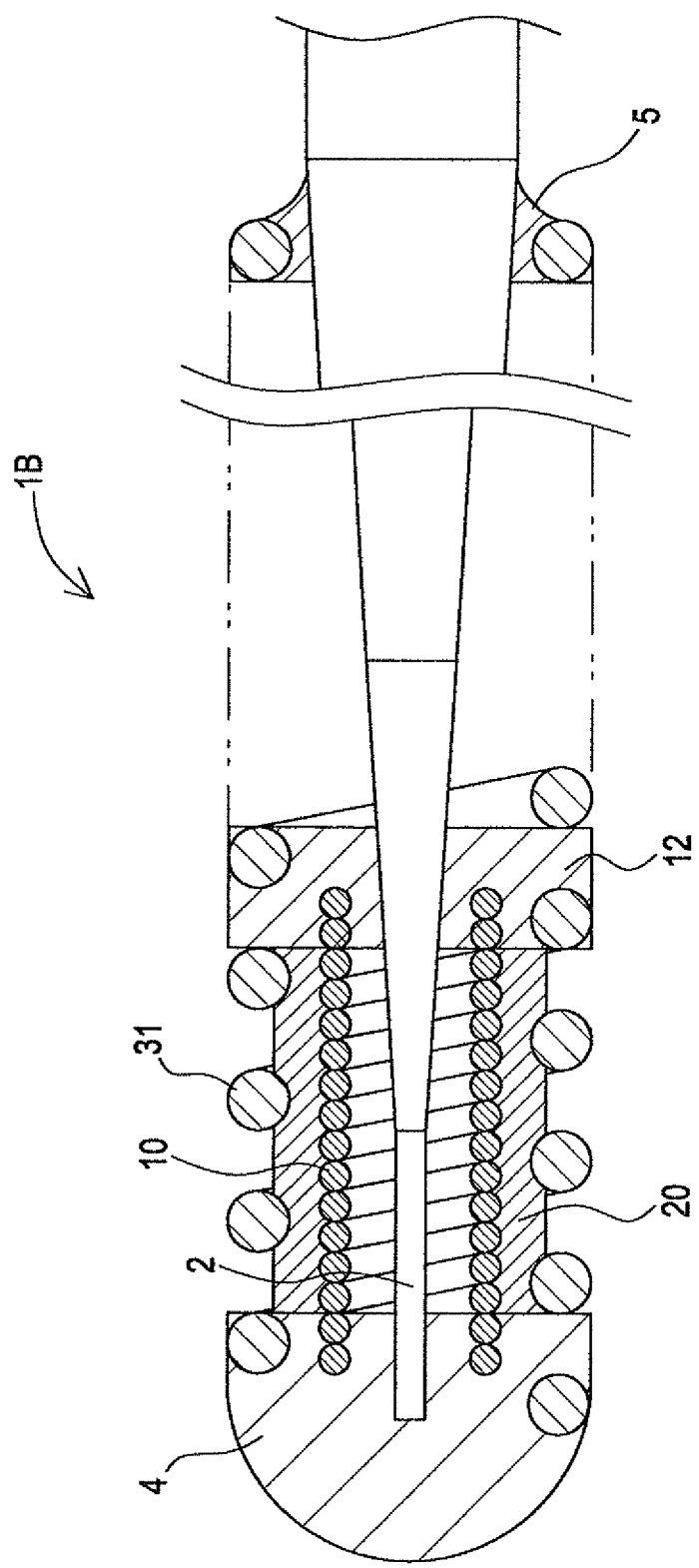
FIG. 2 is an explanatory drawing of a medical guidewire according to a second embodiment.

As illustrated in FIG. 2, at least a front end portion of an outer coiled body 31 is formed in an open coiled manner. A portion of the outer coiled body 31 corresponding to the resin layer 20 is provided with a gap between coil strands.

In this manner, in the case where at least the portion of the outer coiled body 31 corresponding to the resin layer 20 is formed in an open coiled manner, the resin material forming the resin layer 20 can easily be filled in the gap between the coil strands of the outer coiled body 31. Therefore, the resin layer 20 can smoothly be formed. As a result, the productivity of the medical guidewire 1B is remarkably improved. Note that the portion of the outer coiled body 31 corresponding to the resin layer 20 may be entirely formed in an open coiled manner. Alternatively, that portion may be partially formed in an open coiled manner. In other words, the open coiled portion is not strictly limited as long as there is a gap that makes it easy to fill the resin material from outside the outer coiled body 31.

A medical guidewire 1C according to the third embodiment will be described below with reference to FIG. 3. The same elements as those in the first and second embodiments are denoted with the same reference signs and the description thereof is omitted.

Figure 3:
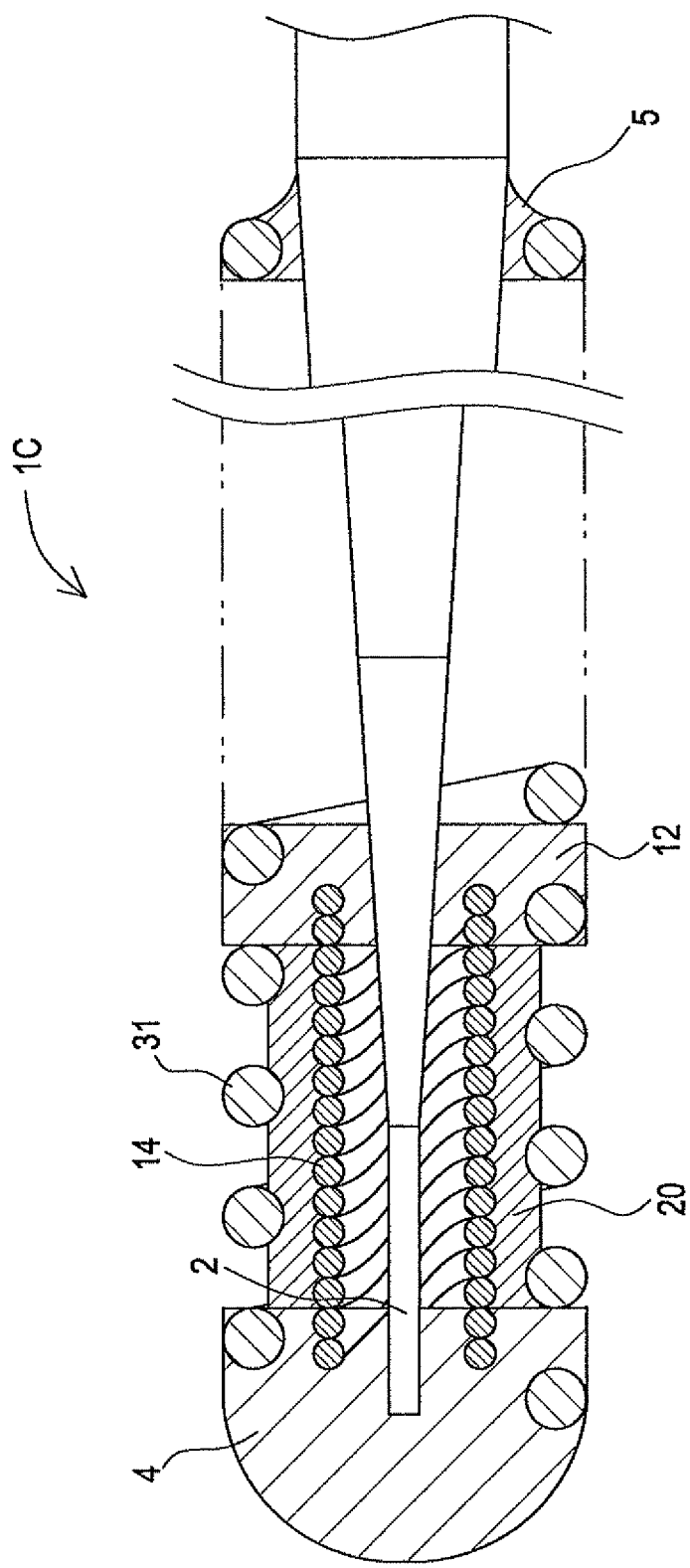
FIG. 3 is an explanatory drawing of a medical guidewire according to a third embodiment.

As illustrated in FIG. 3, an inner coiled body 14 is formed of a multiple-strand coil. The multiple-strand coil has a high robustness due to its property of minimal so-called strand shift, which may occur when the coil is bent or curved.

In the case where the inner coiled body 14 is formed of a multiple-strand coil, the robustness improved by the formation of the resin layer 20 significantly improves the robustness of the front end portion of the medical guidewire 1C. Compared to the configuration using the single coil, the angle of winding the coil strand of the multiple-strand coil relative to the central axis of the medical guidewire 1C is smaller than the angle of winding the coil strand of the single coil relative to the central axis of the medical guidewire. This prevents the mutual interference between the coil strand of the outer coiled body 31 and the coil strand of the inner coiled body 14 in the medical guidewire including the multiple-strand coil. It is thus possible to prevent the coil strand of the inner coiled body 14 from being overlaid on the coil strand of the outer coiled body 31. Therefore, damage to the inner coiled body 14 and the outer coiled body 31 can be avoided, thereby improving the robustness of the medical guidewire 1C. Note that, in addition to the inner coiled body 14, the outer coiled body 31 may be formed of a multiple-strand coil. Alternatively, only the outer coiled body 31 may be formed of a multiple-strand coil. From the viewpoints of ensuring the flexibility of the medical guidewire 1C and making it easy to form the resin layer 20, however, it is most preferable to form only the inner coiled body 14 from a multiple-strand coil.

A medical guidewire 1D according to the fourth embodiment will be described below with reference to FIG. 4. The same elements as those in the first to third embodiments are denoted with the same reference signs and the description thereof is omitted.

Figure 4:
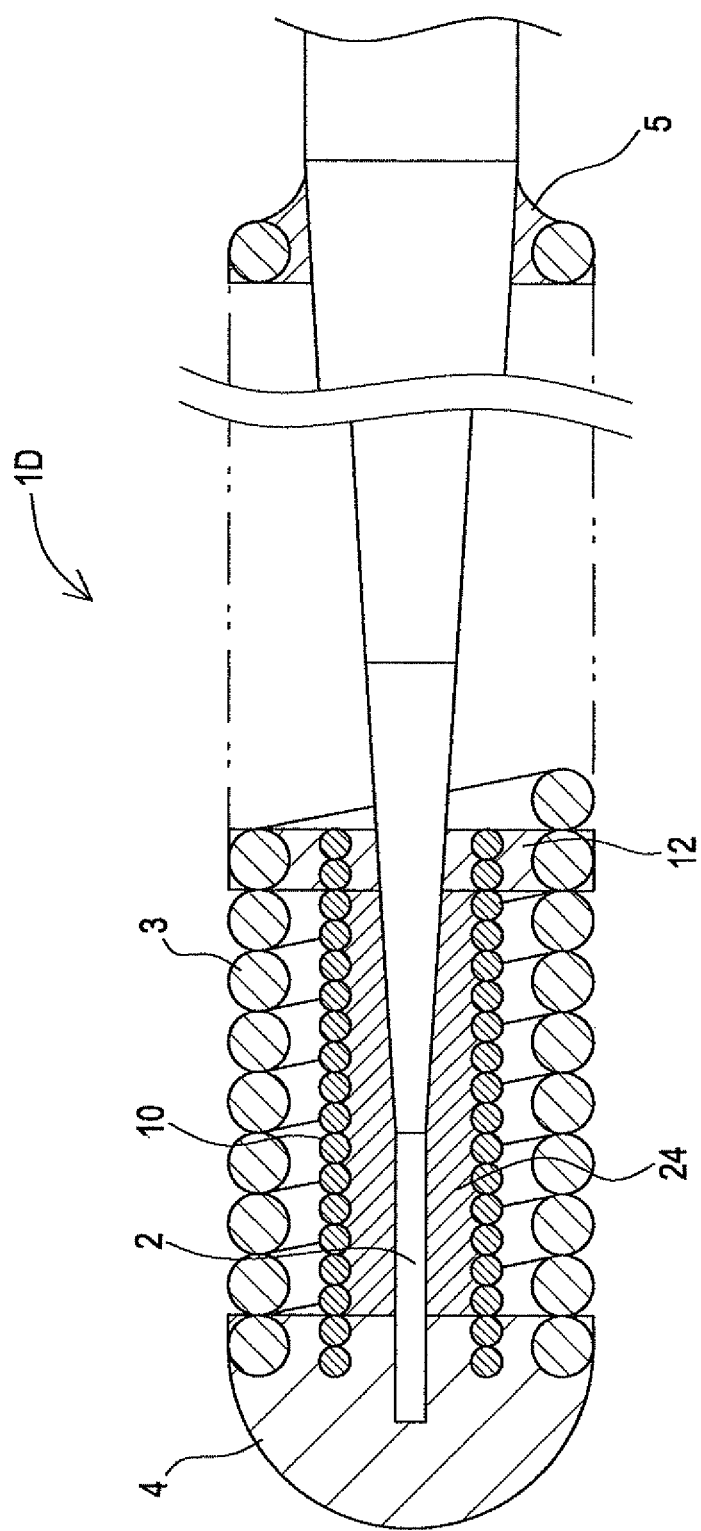
FIG. 4 is an explanatory drawing of a medical guidewire according to a fourth embodiment.

As illustrated in FIG. 4, the medical guidewire 1D includes a core shaft 2, an outer coiled body 3, and an inner coiled body 10. The outer coiled body 3 is formed of a single coil in which at least a front end portion is formed in a close coiled manner. The inner coiled body 10 is formed of a single coil which is close coiled over its entire length.

A space is formed between the core shaft 2 and the inner coiled body 10. This space extends from a most distal portion 4 to a second fixing portion 12. A resin material is filled in this space to thereby form a resin layer 24.

The resin layer 24 between the inner coiled body 10 and the core shaft 2 is formed as follows, for example. That is, before the most distal portion 4 is formed, the resin material is poured between the inner coiled body 10 and the core shaft 2 through an opening formed on the front side of the outer coiled body 3 and the core shaft 2 in the axial direction. Alternatively, the resin layer 24 may be formed by pushing the resin material out of the front side.

The medical guidewire 1D having the above configuration includes the resin layer 24 interposed between the inner coiled body 10 and the core shaft 2. Therefore, even when the inner coiled body 10 and the core shaft 2 are severely bent or curved in use, the inner coiled body 10 and the core shaft 2 can be prevented from coming into contact with each other. Therefore, even when the medical guidewire 1D is curved in use, the mutual interference between the inner coiled body 10 and the core shaft 2 can be prevented, for example. As a result, the core shaft 2 can be prevented from being broken or damaged. In other words, as a whole, the damage of the front end portion of the medical guidewire 1D is prevented and the robustness of the front end portion is improved. Preferably, in the embodiments depicted in FIGS. 4, 6 and 7, the resin layer 24 is provided only between the core shaft 2 and the inner coiled body 10; resin is not provided between the inner coiled body and the outer coiled body 3. This prevents the front end of the medical guidewire from becoming too hard.

A portion of the inner coiled body 10 corresponding to the resin layer 24 is formed in a close coiled manner. Therefore, at the time of forming the resin layer 24 by filling the resin material between the inner coiled body 10 and the core shaft 2, the resin material can be prevented from leaking to the outside of the inner coiled body 10. This makes it possible to reliably form the resin layer 24 inside the inner coiled body 10. It is also possible to reliably prevent the mutual interference between the inner coiled body 10 and the core shaft 2.

Note that at least one of the outer coiled body 3 and the inner coiled body 10 may be formed of a multiple-strand coil. In this case, the multiple-strand coil itself has a high robustness. This in turn improves the robustness of the front end portion of the medical guidewire 1D.

A medical guidewire 1E according to the fifth embodiment will be described below with reference to FIG. 5. The same elements as those in the first to fourth embodiments are denoted with the same reference signs and the description thereof is omitted.

Figure 5:
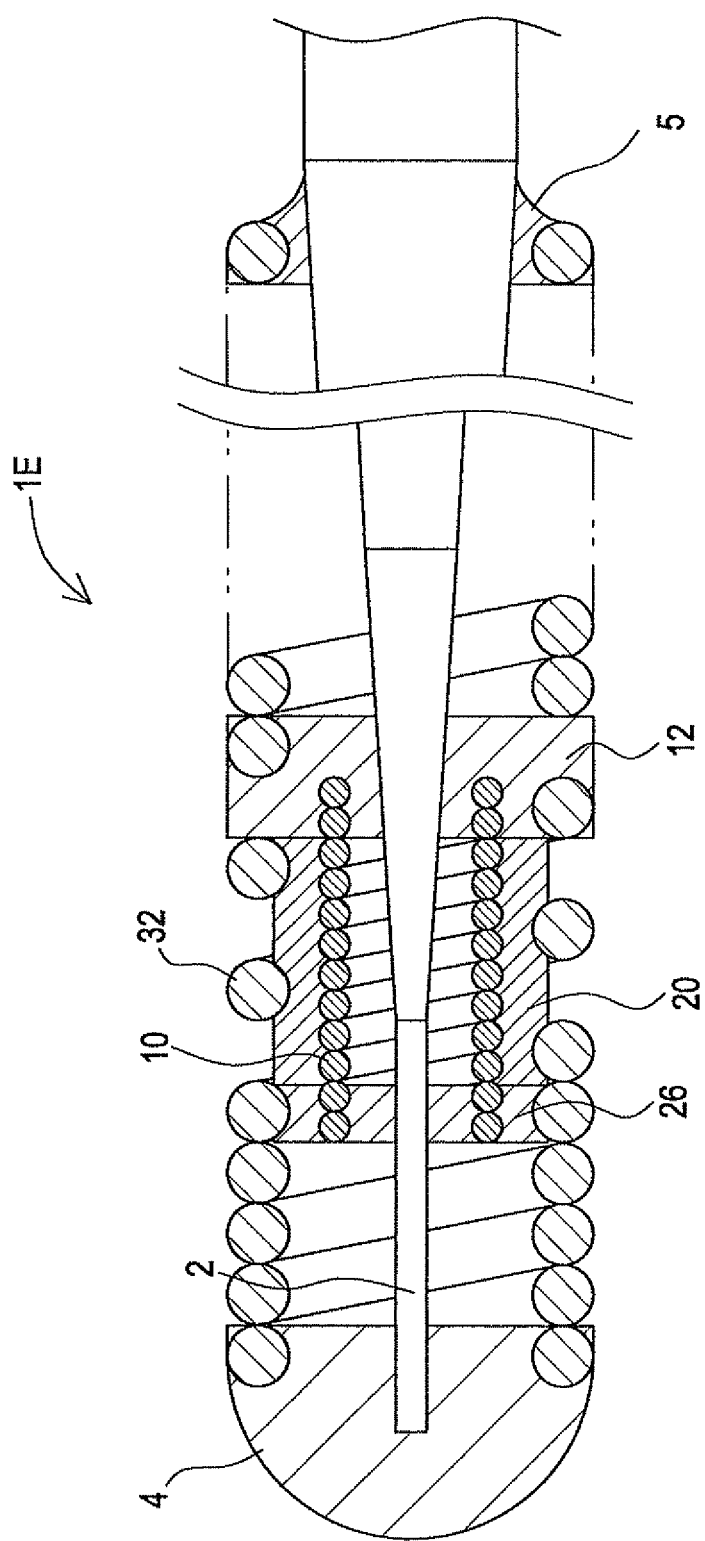
FIG. 5 is an explanatory drawing of a medical guidewire according to a fifth embodiment.

In the medical guidewire 1E illustrated in FIG. 5, an inner coiled body 10 is arranged at a position away from a most distal portion 4, i.e., more toward the proximal end. More specifically, the front end of the inner coiled body 10 is arranged at a position away from the most distal portion 4, i.e., toward the proximal end and connected to a third fixing portion 26 that continues to an outer coiled body 32. The medical guidewire 1E also includes the outer coiled body 32. The outer coiled body 32 includes an open coiled portion and a close coiled portion. The open coiled portion of the outer coiled body 32 is arranged at a position corresponding to the inner coiled body 10.

In this configuration, the front end of the inner coiled body 10 is spaced apart from the most distal portion 4 toward the proximal end. This makes it possible to ensure a sufficient flexibility of the front side of the medical guidewire 1E.

A medical guidewire 1F according to the sixth embodiment will be described below with reference to FIG. 6. The same elements as those in the first to fifth embodiments are denoted with the same reference signs and the description thereof is omitted.

Figure 6:
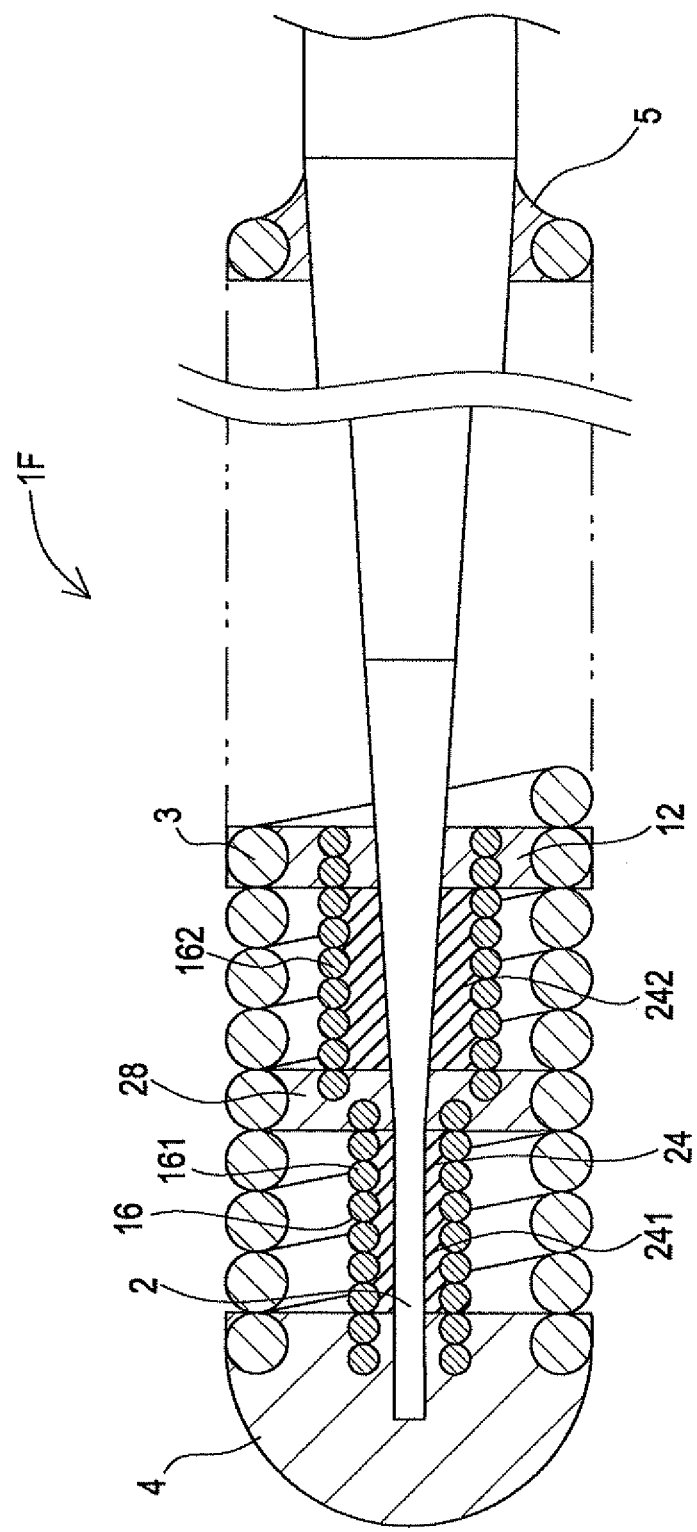
FIG. 6 is an explanatory drawing of a medical guidewire according to a sixth embodiment.

As illustrated in FIG. 6, the medical guidewire 1F includes an inner coiled body 16 having different coil outer diameters between the front side and the proximal side. More specifically, the inner coiled body 16 includes a front-side coil portion 161 and a proximal-side coil portion 162. The front-side coil portion 161 is positioned on the front side of the inner coiled body 16 and has a small coil outer diameter. The proximal-side coil portion 162 is positioned on the proximal side of the inner coiled body 16 and has a larger coil outer diameter than the front-side coil portion 161.

A resin layer 24 is formed between the inner coiled body 16 and a core shaft 2. More specifically, the resin layer 24 includes a thin front-side resin layer 241 and a thick proximal-side resin layer 242. The thin front-side resin layer 241 is formed between the front-side coil portion 161 and the core shaft 2. The thick proximal-side resin layer 242 is formed between the proximal-side coil portion 162 and the core shaft 2.

The resin layer 24 has a smaller thickness on the front side than on the proximal side. Therefore, a much higher flexibility is ensured on the front side of the medical guidewire 1F.

A medical guidewire 1G according to the seventh embodiment will be described below with reference to FIG. 7. The same elements as those in the first to sixth embodiments are denoted with the same reference signs and the description thereof is omitted.

As illustrated in FIG. 7, an inner coiled body 18 of the medical guidewire 1G is formed of a single coil which is open coiled over its entire length.

It is to be understood that the present invention is not limited to the embodiments described above, and that design changes can appropriately be made without departing from the spirit and scope of the invention.

While the disclosed embodiments have been shown and described in detail, the foregoing description is in all aspects illustrative and not restrictive. It is therefore understood that numerous modifications and variations can be devised without departing from the spirit and scope of the invention.

What is claimed is:

1. A medical guidewire comprising:
   a core shaft;
   an outer coiled body covering at least a front end portion of the core shaft; and
   an inner coiled body positioned between the outer coiled body and the core shaft, the inner coiled body covering at least the front end portion of the core shaft,
   wherein a proximal end of the inner coiled body is connected to a fixing portion that continues to the core shaft and the outer coiled body, and a resin material fills a space enclosed by the inner coiled body, the outer coiled body, the fixing portion, and a most distal portion to form a resin layer that is in contact with the outer coiled body, the inner coiled body, the fixing portion, and the most distal portion.

2. The medical guidewire according to claim 1, wherein at least a portion of the inner coiled body that is in contact with the resin layer is densely coiled, such that each coil of the at least a portion of the inner coiled body is in contact with an adjacent coil.

3. The medical guidewire according to claim 1, wherein at least a portion of the outer coiled body that is in contact with the resin layer is sparsely coiled, such that each coil of the at least a portion of the outer coiled body is not in contact with an adjacent coil.

4. The medical guidewire according to claim 2, wherein at least a portion of the outer coiled body that is in contact with the resin layer is sparsely coiled, such that each coil of the at least a portion of the outer coiled body is not in contact with an adjacent coil.

5. The medical guidewire according to claim 1, wherein at least one of the outer coiled body and the inner coiled body is a multiple-strand coil.

6. The medical guidewire according to claim 1, wherein the resin material is hydrophobic.

7. The medical guidewire according to claim 4, wherein an angle of winding the at least a portion of the inner coiled body relative to the core shaft is smaller than an angle of winding the at least a portion of the outer coiled body relative to the core shaft.

8. The medical guidewire according to claim 1, wherein the resin material that contacts the outer coiled body is disposed only on an inner peripheral surface of the outer coiled body.

9. The medical guidewire according to claim 1, wherein the resin material that contacts the inner coiled body is disposed only on an outer peripheral surface of the inner coiled body.

* * * * *